(12) United States Patent
Allen et al.

(10) Patent No.: US 7,632,927 B2
(45) Date of Patent: Dec. 15, 2009

(54) RADIOIMMUNOCONJUGATES FOR TARGETED ALPHA THERAPY

(75) Inventors: Barry Allen, Yowie Bay (AU); Syed Rizvi, Glenfield (AU); Yong Li, Horstville (AU); Chang Fa On, Revesby (AU)

(73) Assignee: The European Community, as Represented by the European Commision (BE)

( * ) Notice: Subject to any disclaimer, the term of this patent is extended or adjusted under 35 U.S.C. 154(b) by 250 days.

(21) Appl. No.: 10/567,813

(22) PCT Filed: Jul. 29, 2004

(86) PCT No.: PCT/EP2004/051663

§ 371 (c)(1),
(2), (4) Date: Sep. 11, 2006

(87) PCT Pub. No.: WO2005/014052

PCT Pub. Date: Feb. 17, 2005

(65) Prior Publication Data

US 2007/0160529 A1    Jul. 12, 2007

(30) Foreign Application Priority Data

Aug. 11, 2003 (AU) ............................. 2003904201

(51) Int. Cl.
*C07K 17/00*     (2006.01)
(52) U.S. Cl. ................................ 530/391.1; 424/178.1
(58) Field of Classification Search ........................ None
See application file for complete search history.

(56) References Cited

FOREIGN PATENT DOCUMENTS

WO    WO 02/22685    3/2002

OTHER PUBLICATIONS

Allen et al. (Crit. Rev. Oncol. Hematol. vol. 39(1-2), pp. 139-146), 2001).*
Denton et al. (Br. J. Cancer, vol. 76(5), pp. 614-621, 1997).*
Allen et al. (Crit. Rev. Oncol. Hematol. vol. 39(1-2), pp. 139-146), 2001) Abstract only.*
Denton et al. (Br. J. Cancer, vol. 76(5), pp. 614-621, 1997) Abstract only.*
Murray et al. (J of Nuclear Medicine, vol. 42, pp. 726-732, 2001).*
Allen et al. (Critical Reviews in Onc./Hematology, vol. 39, pp. 139-146, 2001).*
Perkins Alan et al; "Antibody conjugate radioimmunotherapy of superficial bladder cancer."; Brazilian Archives of Biology and Technology; vol. 45, No. Special Issue, Sep. 2002, pp. 87-89, XP001204515; ISSN: 1516-8913.
Lo Benny: "Biotherapy" European Journal of Cancer, Pergamon Press, Oxford, GB, vol. 37, Oct. 2001, p. 228, XP004359247; ISSN: 0959-8049.
Seyed K I: "Advancements in cancer therapy with alpha-emitters: a review" International Journal of Radiation: Oncology Biology Physics, Pergamon Press, US, vol. 51, No. 1, Sep. 1, 2001, pp. 271-278, XP002206123; ISSN: 0360-3016.

* cited by examiner

*Primary Examiner*—Larry R. Helms
*Assistant Examiner*—Meera Natarajan
(74) *Attorney, Agent, or Firm*—Cantor Colburn LLP

(57) ABSTRACT

A radioimmunoconjugate for targeted alpha therapy comprises an alpha-emitter (e.g. Bi-213) linked to the monoclonal antibody C595. This radioimmunoconjugate is widely applicable in cancer therapy and is particularly efficient for treatment of pancreatic and prostate cancer, as well as for breast and ovarian cancer.

22 Claims, No Drawings

RADIOIMMUNOCONJUGATES FOR TARGETED ALPHA THERAPY

TECHNICAL FIELD

The present invention generally relates to radioimmunoconjugates for targeted alpha-immunotherapy.

BACKGROUND ART

The treatment of cancer by radio-immunotherapy involves injecting the patient with a radioactive isotope 'bullet' connected to a specific cancer cell vector such as a monoclonal antibody, with the aim of selectively destroying targeted tumour cells. During radioactive decay, photons, electrons or even heavier particles are emitted and damage or kill cells along their trajectory.

Radio-immunotherapy (RIT) is still a relatively new modality for cancer therapy, which started using beta-emitting radionuclides. These have a relative low linear energy transfer (LET) and a long range in tissues, so their decay energy is only partially absorbed by the cancerous cells; the remainder attacks healthy cells in an undesirable manner.

As a result, the focus of research shifted to radionuclides emitting alpha particles, which have high linear energy transfer values and release their energy over just a few cell diameters. Recent experiments have proved alpha emitters to be very effective in destroying tumour cells. They are considered to be especially attractive for the treatment of blood-borne cancers and micrometastatic tumours (where cancer cells are typically present throughout the body). Another likely area of use for alpha-immunotherapy is in treating the small numbers of cancer cells that may remain after high-dose chemotherapy or surgery.

RIT is performed by administering to cancer patients so-called radioimmunoconjugates, which are constructs comprising a radionuclide with desirable properties linked to an antibody. Generally, the linking of the radionuclide to the antibody is done by means of a chelating agent. In the body, the antibody will carry the radionuclide to a diseased tissue expressing a corresponding antigen.

To date, a variety of alpha-emitting radionuclides have been used for RIT and more particularly: terbium-149 (Tb-149), astatine (At-211), bismuth-212 (Bi-212), bismuth-213 (Bi-213) and actinium-225 (Ac-225). Furthermore, a variety of chelating agents and antibodies, especially monoclonal antibodies, have been developed.

The development of radioimmunoconjugates involves adequate selections of radionuclides, targeting moieties and chelators. When designing a radioimmunoconjugate for RIT, numerous parameters have to be taken into account, in particular the targeting specificity of the antibody to the cells to be targeted, the cytotoxic potentiality of the selected radionuclide with regard to the targeted cells and the stability of the antibody-radionuclide link by the chelator. The design of radioimmunoconjugates is thus a complex matter and the actual efficiency of a radioimmunoconjugate can in fact only be validated by testing in pre-clinical and clinical trials.

Among the radionuclides, Bi-213 is currently widely used in RIT. This radionuclide decays mainly (98%) by β- and 440 keV γ emission with a half-life of 45.6 minutes to the ultra-short lived high-energy (8.375 MeV) alpha-emitter polonium-213 ($t_{1/2}$ of 4 μs), whereas a direct alpha-decay pathway to thallium-209 plays only a negligible role (2% of all Bi-213 decays).

U.S. Pat. No. 5,641,471 discloses a method for preparing Bi-213 for therapeutic use, wherein a monoclonal antibody is used as targeting moiety. A chelator such as CHX-DTPA (cyclohexyldiethylenetriamine pentaacetic acid) is attached to the antibody and functions to chelate the radionuclide. In this manner, the radioisotope is delivered to the target cell where it can function in a therapeutic manner to destroy it.

U.S. Pat. No. 5,246,691 discloses radioimmunotherapy using Ac-225 and its daughters as part of a radioimmunoconjugate also comprising an antibody such as human monoclonal antibody and humanized antibodies.

Many references have described the use of radioimmunoconjugates comprising a radionuclide linked to a monoclonal antibody by a chelator. Although increasing efforts are made in RIT and despite the growth of monoclonal antibodies used in clinical trials, there is a continuous need for radioimmunoconjugates providing efficient therapeutic effects in cancer therapy.

GENERAL DESCRIPTION OF THE INVENTION

A radioimmunoconjugate in accordance with the present invention comprises an alpha-emitting radionuclide bound to the monoclonal antibody C595. The monoclonal antibody C595 recognises a tetrapeptide motif in the protein core of MUC-1 mucin. As known from the literature, it is an IgG3 type monoclonal antibody raised against the protein core of human urinary epithelial mucin.

It will be appreciated that during the development of the present invention, it has been observed that the MUC-1 receptor is expressed on many different cancer cell types and that the C595 antibody permits the targeting of a particular epitope of the MUC-1 that is not expressed on normal cells. Furthermore, it has been found that the present radioimmunoconjugate permits an efficient targeting of the MUC-1 receptor expressed on cancer cells as well as improved therapeutic efficiency.

It has also surprisingly been found that the MUC-1 receptor is particularly present on human prostate and pancreatic cancer cells and that the radioconjugate of the invention allows the killing of those cancer cells with a very high efficacy.

A further surprising and advantageous aspect of the present invention is that the radioconjugate does not target stem cells.

The present radioimmunoconjugate is thus of wide applicability in cancer treatment for its high targeting specificity and cytotoxicity. This is an important advantage of the present invention since it provides a radioimmunoconjugate that can be used in several cancer types with high therapeutical efficacy.

It is to be noted that the radioimmunoconjugate of the invention finds particular application in the therapeutical treatment of prostate and pancreatic cancers.

Additionally, it is of particular interest in the treatment of breast and ovarian cancer.

It is to be further noted that the present radioimmunoconjugate is of particular applicability for adjunctive therapy for early metastatic cancer, or cancer at the minimum residual stage. For example, high risk cancer patients shall be treated with the radioimmunoconjugates immediately after removal of the primary tumour to selectively kill isolated cancer cells or small nests of such cells at the preangiogenic stage, where rapid uptake and incorporation can occur.

Radionuclides to be used in the radioimmunoconjugate of the invention are preferably selected from the list comprising: Tb-149, At-211, Bi-212 and Bi-213. These radionuclides have suitable radiation properties and their relatively short half-life allows the preparation of stable radioimmunoconjugates permitting a rapid delivery of the radiation doses.

Bi-213 ($t_{1/2}$=46 min) and Tb-149 ($t_{1/2}$=4 h) are however particularly preferred radionuclides. As is well known, Bi-213 can be obtained by radioactive decay of the mother radionuclide Ac-225. Preparation of Bi-213 is typically carried out by elution from a separation column (generally referred to as radionuclide generator) loaded with the mother radionuclide Ac-225.

In some applications, it may be desirable to employ an alpha-emitting radionuclide having a longer half-life (e.g. of several days) than the above mentioned alpha-emitting radionuclides. In such a case, one may employ the relatively long-lived radionuclide Ac-225 ($t_{1/2}$=10 d) for the preparation of the radioimmunoconjugate according to the invention. As is well known, two major routes for the production of Ac-225 have been developed: via Th-229 and via Ra-226.

Any method for producing the radionuclides can be employed, as long as it provides the desired radionuclide with a sufficient purity for medical application.

The binding (also referred to as coupling or linking) of the radionuclide to the monoclonal antibody can be done in any suitable way, as long as the targeting specificity of the monoclonal antibody is not hampered to a substantial amount. Accordingly, the binding may be done through one of the now many known chelating agents. Particularly preferred chelating agents are DOTA, cDTPA, TETA or CHX-A-DTPA.

The present invention also provides a method for manufacturing a radioimmunoconjugate, wherein an alpha-emitting radionuclide is bound to the monoclonal antibody C595.

Viewed from another aspect, the invention provides the use of a radioimmunoconjugate in the manufacture of a radiopharmaceutical for cancer therapy, and more specifically for the therapeutic treatment of breast, prostate, ovarian and/or pancreatic cancer. Additionally the radiopharmaceutical may comprise a pharmaceutically acceptable carrier (e.g. a liquid) and/or excipient and/or diluent.

According to a further aspect of the invention, a method of treatment of a mammal affected by a cancer is proposed, which comprises administering to the mammal a therapeutically effective amount of the present radiopharmaceutical.

The present method is of wide applicability for cancer treatment and is particularly suited for treatment of breast, prostate, ovarian and pancreatic cancer. It will however be appreciated that the radioconjugates, respectively radiopharmaceuticals, of the invention find particular application in adjunctive therapy for early stage metastatic cancer, or cancer at the minimum residual disease stage.

The method may thus comprise the administration of the radiopharmaceutical directly after removal of a primary tumour or upon detection of tumour cell nests (i.e. regions of tumour cells) at the preangiogenic stage.

Alternatively, the method according to the invention may use risk factors determined from a number of clinical and laboratory parameters (such as cancer serum proteins) to determine the time point of administering the radiopharmaceutical. Accordingly, the administration of the radiopharmaceutical may be carried out in the context of diagnosis of high risk factors in a cancer patient and/or on detection of certain known cancer proteins in serum, e.g. PSA, Ca125 or MIA.

DETAILED DESCRIPTION OF PREFERRED EMBODIMENTS

The present radioimmunoconjugate combines an alpha-emitting radioisotope (e.g. Tb-149, At-211, Bi-212, Bi-213 or Ac-225) with a monoclonal antibody against the MUC-1 receptor. A merit of the present invention is to have found a specific combination of radionuclide and antibody for RIT, which allows the killing of individual cancer cells with a very high efficacy and thus results in improved therapeutic effect.

It is to be appreciated that the present radioimmunoconjugate proves advantageous in many respects. The monoclonal antibody C595 has high selectivity to cancer cells as MUC-1 is highly expressed on many cancer cells. C595 can be stably bonded to alpha-emitting radionuclides by known chelating agents. Alpha radiation kills cancer cells in 2-3 nuclear hits. The range of the emitted alpha particles are three to five times the diameter of a cancer cell, so the radiation dose is specific to small clusters of cancer cells. Additionally, alpha radiation spares capillary endothelial cells. The half-life of the proposed alpha-emitters is suitable for preparation and the stability of the radioimmunoconjugate. Also, the short half-life is suitable for killing of isolated cancer cells and preangiogenic lesions. The use of alpha-emitters also results in low concomitant radiation dose to normal tissue. Overall, the use of the present radioimmunoconjugates in cancer treatment permits a high therapeutic ratio, and will provide an improved prognosis for survival by treatment of micrometastases in subclincial, early stage metastatic disease or at the minimum residual disease stage.

The treatment using the present radioimmunoconjugates permits to overcome many deficiencies of prior art methods. Specifically, radiocolloid therapy is not suitable for adjunctive therapy as it is not selective of cancer cells. Beta and gamma emitting radionuclides have been coupled to specific monoclonal antibodies against cancer cells. For example, beta-emitting radioimmunoconjugates with I-131, In-111, Y-90 etc. have been synthesized but are relatively ineffective in therapy. Chemotherapy drugs are a systemic therapy but mostly are incapable of eliminating the disease.

As already mentioned, the present radioimmunoconjugate combines an alpha-emitting radionuclide and C595, and has high targeting specificity and cytotoxicity. The radioimmunoconjugate is particularly efficient for targeting and killing tumor cells in the case of prostate, pancreatic, ovarian and breast cancer.

As it will appear from the examples below, the production of the present radioimmunoconjugates can be carried out using conventional materials. The production and purification procedures for the preferred isotopes are well known. The preferred chelating agents are commercially available. The monoclonal antibody C595 was obtained from the University of Nottingham, UK.

EXAMPLES a) Production of the Radionuclides

The rare earth nuclide Tb-149 can be produced on a tandem, cyclotron or linear accelerator using high energy heavy ions such as boron or carbon or nitrogen ions to bombard targets of Praseodymium, e.g. Pr($^{12}$C,4n) or Neodymium Nd($^{12}$C,5n) or at GeV energies using proton induced spallation.

At-211 can be produced with 26 MeV alphas bombarding a Bi target.

Bi-213 is available from the decay of the mother radioisotope Ac-225. This is typically done by loading the mother radionuclide Ac-225 on a separation column (employing ion exchange resin or extraction chromatographic material) of a so-called radionuclide generator.

Bi-212 is available from the decay of the parent radioisotope Th-228.

Ac-225 can be obtained by neutron or proton bombardment of Ra-226 targets (see e.g. EP 0 752 710-B1 and EP 0

962 942-B1). Alternately, Ac-225 can be obtained by radioactive decay of Th-229, which itself can be produced by irradiation of Th-232 in a reactor.

b) Purification of the Radionuclides

For the preparation of Tb-149 radionuclides of high purity, Tb-149 was separated from the irradiated, thick target of Praseodymium by dissolution in 6 M nitric acid. The sample was then irradiated to dryness and yield determined by gamma ray spectroscopy. The residue was dissolved in 0.16 M hydroxyisobutyric acid and passed through a cation exchange column (particle size 13 μm). The pH of the eluent was adjusted to 5 by aqueous ammonia. Elution was carried out under a pressure of 7 kg·cm$^{-2}$ at a flow rate of 0.5 mL·min$^{-1}$. Terbium fractions were dried gently and healed to 450 degrees to destroy the Tb-isobutyrate complex. The residue was dissolved in dilute nitric or hydrochloric acid for the radiolabelling (conjugation) procedure, wherein Tb-149 is bound to the mAb C595.

The preparation of Bi-213 for therapeutic use has been done by elution from a separation column loaded with the parent radionuclide Ac-225 with hydroiodic acid, as is known in the art.

c) Radioimmunoconjugate Production

Different radioimmunoconjugates have been produced by binding the purified radionuclides Tb-149 or Bi-213 to the monoclonal antibody C595 by means of conventional chelating agents. Preferred chelating agents are DOTA (1,4,7,10-tetraazacyclododecane-N,N',N'',N'''-tetraacetic acid); DTPA (diethylenetriaminepentaacetic acid) and its derivatives (e.g. benzyl-DTPA, MX-DTPA (tiuxetan), cyclohexyl-DTPA), in particular cyclohexyl-DTPA and CHX-A-DTPA; TETA (1,4,8,11-tetraazacyclotetradecane N,N',N'',N'''-tetraacetic acid).

d) Results

Radioimmunoconjugates of the C595 mAb bound to Tb-149 or Bi-213 have been produced according to the above-described procedures. Their labelling (coupling) efficiency has been verified with prostate, pancreatic and other cancers (>90%), in vitro cell survival and in vivo biodistribution in nude mice with tumour xenografts.

Bi-213-labelled C595 has been found to be cytotoxic in vitro in many different cancer cell lines, and to be surprisingly effective in inhibiting tumour growth in a range of in vivo cancer models, especially prostate, pancreatic and ovarian cancers. It was not effective in bladder cancer, which was the original application of C595. Tumour growth was inhibited using the two-day post-inoculation model, where the lesion was preangiogenic, and comprised isolated cells and cell clusters. Local injection gave complete inhibition of tumour growth, systemic injection did so at the higher injected doses, but within the maximum tolerance dose for the alpha-immunoconjugate.

The invention claimed is:

1. Radioimmunoconjugate comprising an alpha-emitting radionuclide bound to a monoclonal antibody, wherein said monoclonal antibody is C595.

2. Radioimmunoconjugate according to claim 1, wherein said alpha-emitting radionuclide is selected from the group comprising: Tb-149, At-211, Bi-212, Bi-213 and Ac-225.

3. Radioimmunoconjugate according to claim 2, wherein said alpha-emitting radionuclide is Bi-213 or Tb-149.

4. Radioimmunoconjugate according to claim 2, wherein said alpha-emitting radionuclide is Ac-225.

5. Radioimmunoconjugate according to claim 1, wherein said alpha-emitting radionuclide is bound to said monoclonal antibody by a chelating agent.

6. Radioimmunoconjugate according to claim 5, wherein said chelating agent is DOTA, cDTPA, DTPA-CHX-A or TETA.

7. Radioimmunoconjugate according to claim 1, for use in therapy of breast, prostate, ovarian and/or pancreatic cancer.

8. Method for manufacturing a radioimmunoconjugate, wherein an alpha-emitting radionuclide is bound to a monoclonal antibody, said monoclonal antibody being C595.

9. Radiopharmaceutical for cancer therapy comprising a radioimmunoconjugate of an alpha-emitting radionuclide bound to a monoclonal antibody, wherein said monoclonal antibody is C595.

10. Radiopharmaceutical according to claim 9, wherein said alpha-emitting radionuclide is selected from the group comprising: Tb-149, At-211, Bi-212, Bi-213 and Ac-225.

11. Radiopharmaceutical according to claim 9, comprising a pharmaceutically acceptable carrier and/or diluent and/or excipient.

12. Radiopharmaceutical according to claim 9, wherein said cancer is breast, prostate, ovarian or pancreatic cancer.

13. Method of treatment of a mammal affected by a cancer which comprises administering to said mammal a therapeutically effective amount of a radiopharmaceutical comprising an alpha-emitting radionuclide bound to a monoclonal antibody, said monoclonal antibody being C595.

14. Method according to claim 13, wherein said alpha-emitting radionuclide is selected from the group comprising: Tb-149, At-211, Bi-212, Bi-213 and Ac-225.

15. Method according to claim 13, wherein said cancer is one of breast, prostate, ovarian and pancreatic cancer.

16. Method according to claim 15, wherein said alpha-emitting radionuclide is selected from the group comprising: Tb-149, At-211, Bi-212, Bi-213 and Ac-225.

17. Method according to claim 15, wherein said alpha-emitting radionuclide is Bi-213 or Tb-149.

18. Method according to claim 13, wherein said radiopharmaceutical is administered as an adjunctive therapeutic treatment.

19. Method according to claim 13, wherein said radiopharmaceutical is administered directly after removal of a primary tumour.

20. Method according to claim 13, wherein said radiopharmaceutical is administered upon detection of regions of tumour cells at the preangiogenic stage.

21. Method according to claim 13, wherein said radiopharmaceutical is administered upon diagnosis of high risk factors in said mammal.

22. Method according to claim 13, wherein said radiopharmaceutical is administered upon detection of certain cancer proteins in serum.

* * * * *